US009610456B2

(12) United States Patent
Linke et al.

(10) Patent No.: US 9,610,456 B2
(45) Date of Patent: Apr. 4, 2017

(54) NANOWIRE-BASED DEVICES FOR LIGHT-INDUCED AND ELECTRICAL STIMULATION OF BIOLOGICAL CELLS

(71) Applicant: QUNANO AB, Lund (SE)

(72) Inventors: Heiner Linke, Lund (SE); Christelle Prinz, Lund (SE); Gaelle Piret, Lund (SE); Jonas Ohlsson, Lund (SE); Maria Thereza Perez, Lund (SE)

(73) Assignee: NEURONANO AB, Karlshamn (SE)

( * ) Notice: Subject to any disclaimer, the term of this patent is extended or adjusted under 35 U.S.C. 154(b) by 56 days.

(21) Appl. No.: 14/361,446

(22) PCT Filed: Nov. 29, 2012

(86) PCT No.: PCT/IB2012/002936
§ 371 (c)(1),
(2) Date: May 29, 2014

(87) PCT Pub. No.: WO2013/080052
PCT Pub. Date: Jun. 6, 2013

(65) Prior Publication Data
US 2014/0330337 A1   Nov. 6, 2014

Related U.S. Application Data

(60) Provisional application No. 61/565,041, filed on Nov. 30, 2011.

(51) Int. Cl.
*A61N 1/378* (2006.01)
*A61N 1/36* (2006.01)
(Continued)

(52) U.S. Cl.
CPC ......... *A61N 1/3787* (2013.01); *A61N 1/0543* (2013.01); *A61N 1/36046* (2013.01);
(Continued)

(58) Field of Classification Search
CPC ................ A61N 1/3787; A61N 1/0543; A61N 1/36046; A61N 1/36125; B82Y 10/00; H01L 31/035227; H01L 31/042; H01L 31/075
(Continued)

(56) References Cited

U.S. PATENT DOCUMENTS 7,682,943 B2   3/2010 Samuelson et al.
7,829,443 B2  11/2010 Seifert et al.
(Continued)

FOREIGN PATENT DOCUMENTS

EP          1864690 A2     12/2007
WO   WO 2008-141271 A1    11/2008
(Continued)

OTHER PUBLICATIONS

Verma et al. ("Gigaohm resistance membrane seals with stealth probe electrodes".*
(Continued)

*Primary Examiner* — Carl H Layno
*Assistant Examiner* — Erin M Piateski
(74) *Attorney, Agent, or Firm* — The Marbury Law Group PLLC

(57) ABSTRACT

A device including at least one photovoltaic cell and at least one nanowire configured to electrically stimulate a biological material in response to radiation.

16 Claims, 13 Drawing Sheets

(51) Int. Cl.
*H01L 31/042* (2014.01)
*H01L 31/0352* (2006.01)
*B82Y 10/00* (2011.01)
*H01L 31/075* (2012.01)
*A61N 1/05* (2006.01)
*H01L 51/00* (2006.01)
*H01L 51/42* (2006.01)
*B82Y 5/00* (2011.01)

(52) U.S. Cl.
CPC .......... *A61N 1/36125* (2013.01); *B82Y 10/00* (2013.01); *H01L 31/035227* (2013.01); *H01L 31/042* (2013.01); *H01L 31/075* (2013.01); *A61N 1/0534* (2013.01); *B82Y 5/00* (2013.01); *H01L 51/0093* (2013.01); *H01L 51/42* (2013.01); *Y02E 10/548* (2013.01)

(58) Field of Classification Search
USPC .......................................................... 607/45
See application file for complete search history.

(56) References Cited

U.S. PATENT DOCUMENTS

| | | | |
|---|---|---|---|
| 2006/0263255 A1* | 11/2006 | Han | B82Y 10/00 422/83 |
| 2008/0288067 A1* | 11/2008 | Flood | A61N 1/0543 623/6.63 |
| 2009/0011536 A1 | 1/2009 | Zhang et al. | |
| 2010/0211146 A1 | 8/2010 | Strowbridge et al. | |
| 2010/0249877 A1* | 9/2010 | Naughton | B82Y 20/00 607/54 |
| 2012/0222970 A1 | 9/2012 | Melosh et al. | |
| 2013/0098288 A1 | 4/2013 | Samuelson et al. | |
| 2013/0203242 A1 | 8/2013 | Samuelson et al. | |

FOREIGN PATENT DOCUMENTS

| | | |
|---|---|---|
| WO | WO 2009-067668 A1 | 5/2009 |
| WO | WO 2009-104056 A1 | 8/2009 |
| WO | WO 2011-038228 A1 | 3/2011 |
| WO | WO 2011-078780 A | 6/2011 |
| WO | WO 2011-142717 A1 | 11/2011 |
| WO | WO 2011-163262 A2 | 12/2011 |

OTHER PUBLICATIONS

International Search Report and Written Opinion received in connection with international application No. PCT/IB2012/002936, dated Aug. 22, 2013.
International Preliminary Report on Patentability received in connection with international applicaton No. PCT/IB2012/002936, dated Jun. 3, 2014.
Khraiche et al., "Ultra High Photosensitivity Silicon Nanophotonics for Retinal Prosthesis: electrical Characteristics", Conf. Proc IEEE Eng. Med. Biol. Soc., 2933-6 (2011).
Nirenberg et al., "Retinal prosthetic strategy with the capacity to restore normal vision", PNAS, vol. 109 (37), pp. 15012-15017 (Sep. 11, 2012).
Piret et al., Neurite outgrowth synaptohysin expression of postnasal CNS neurons on GaP nanowire arrays in long-term retinal cell culture, Biomaterials, vol. 34(4), (2012), available online at: http://dx.doi.org/10.1016/j.biomaterials.2012.10.042.
Verma et al., "Gigaohm resistance membrane seals with probe electrodes", Appl. Phys. Lett., vol. 97(3), 033704 (2010).

* cited by examiner

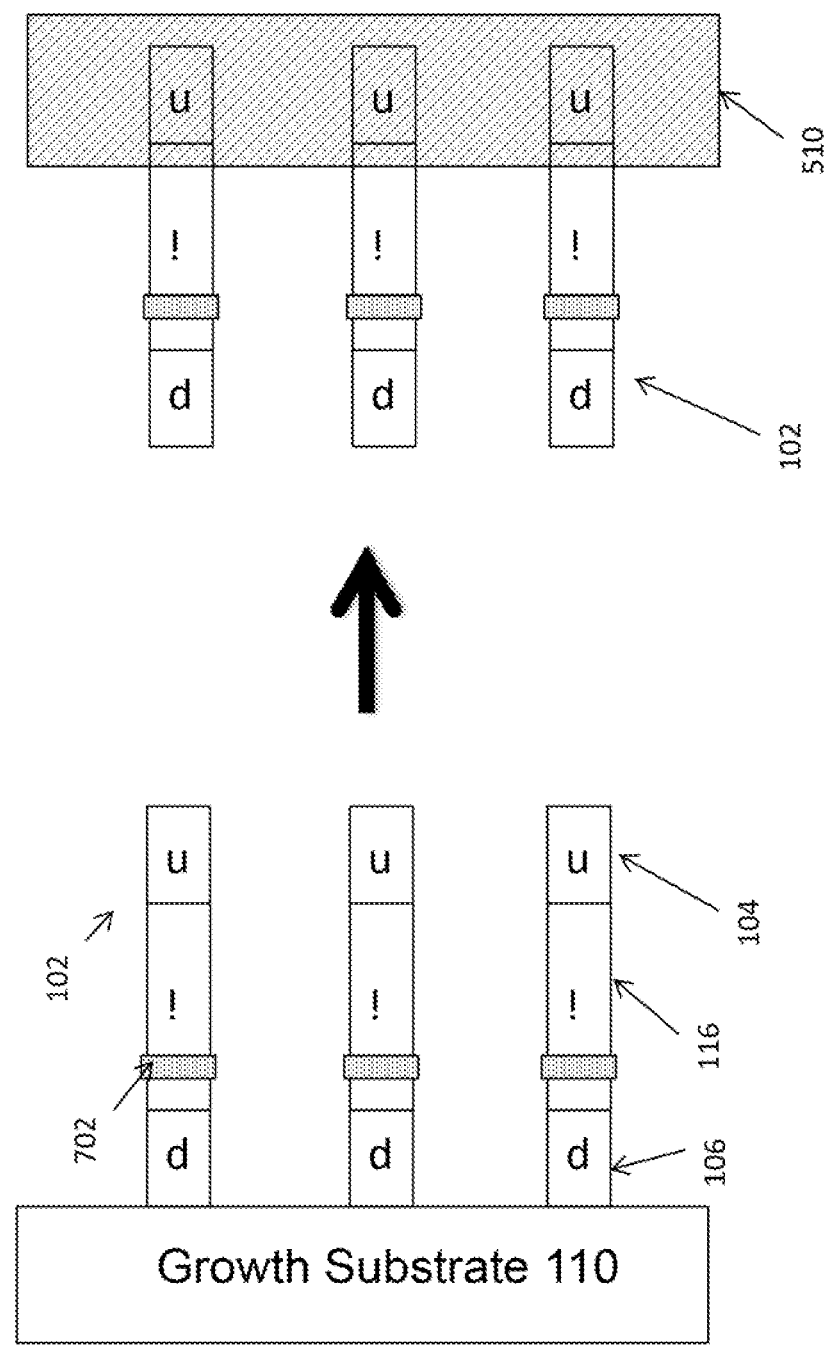

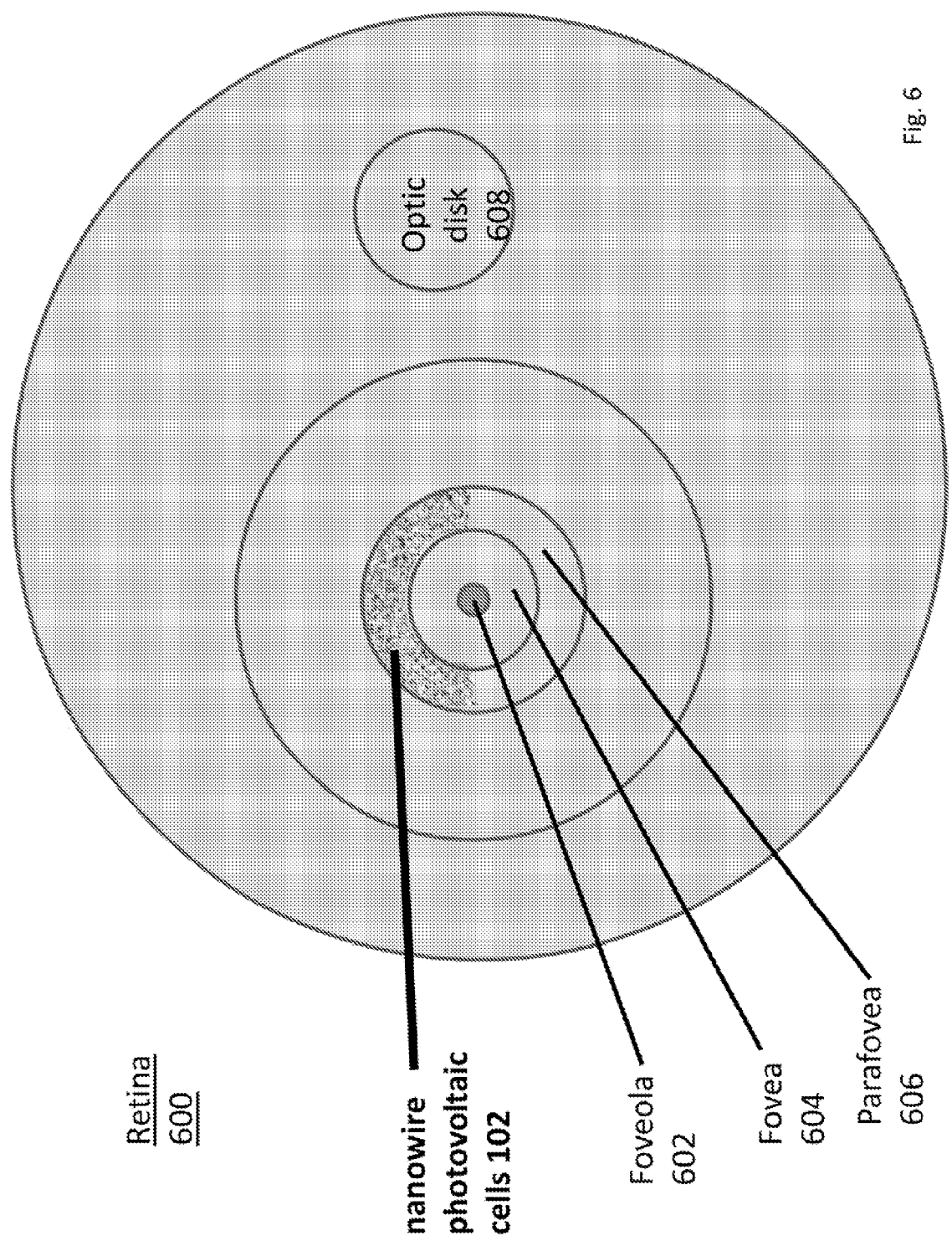

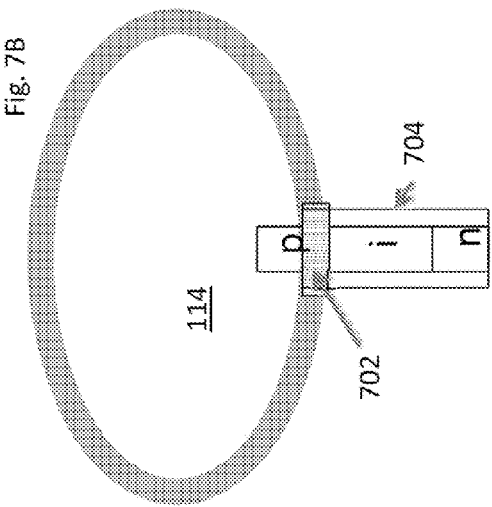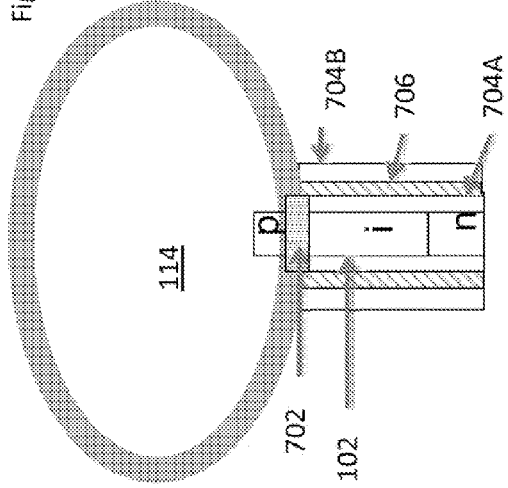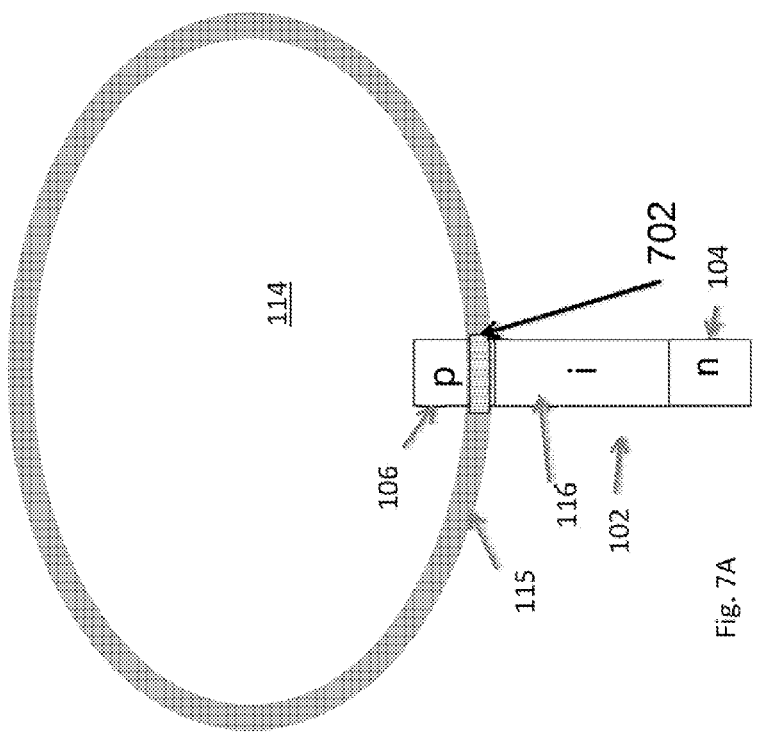

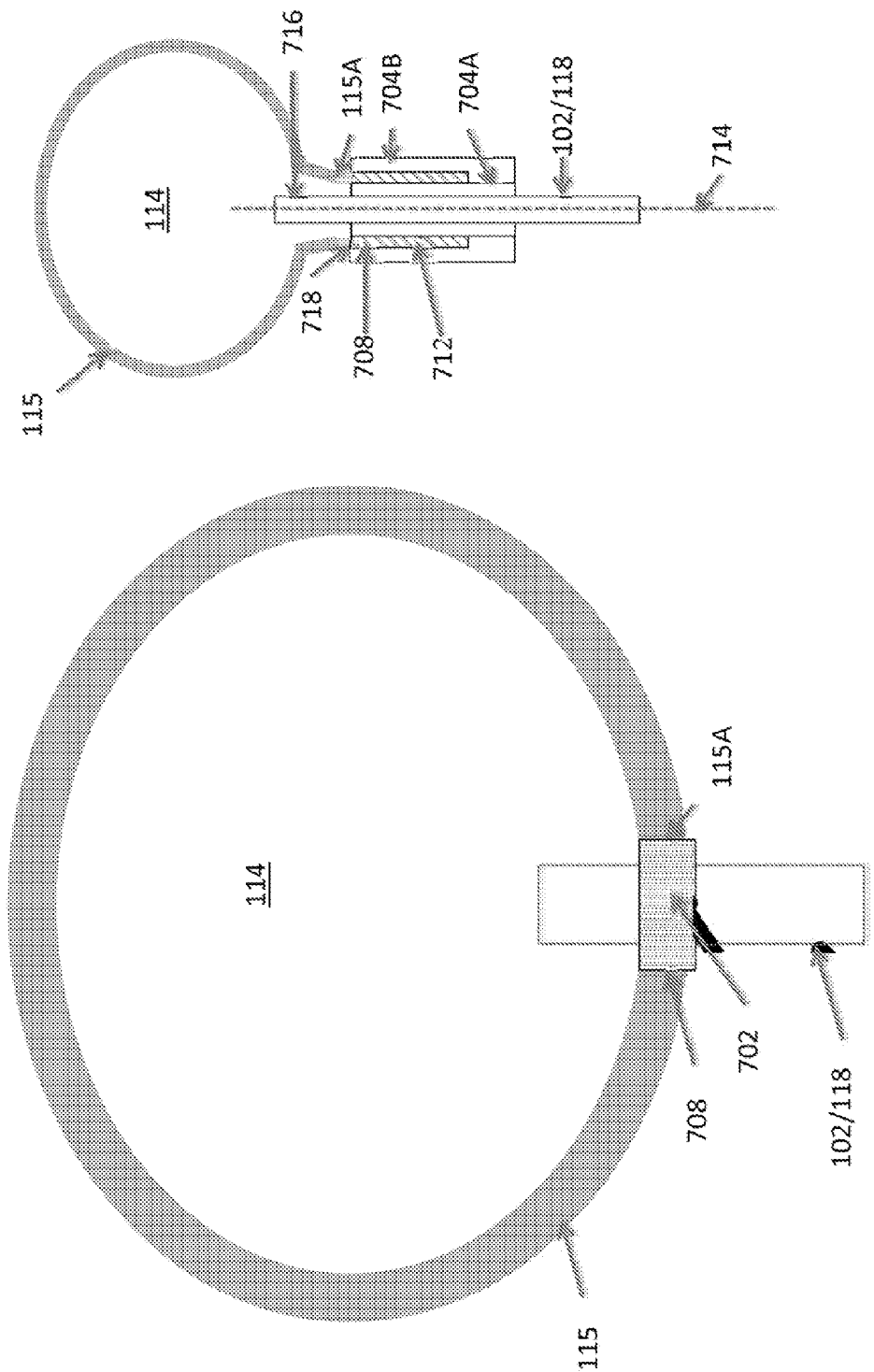

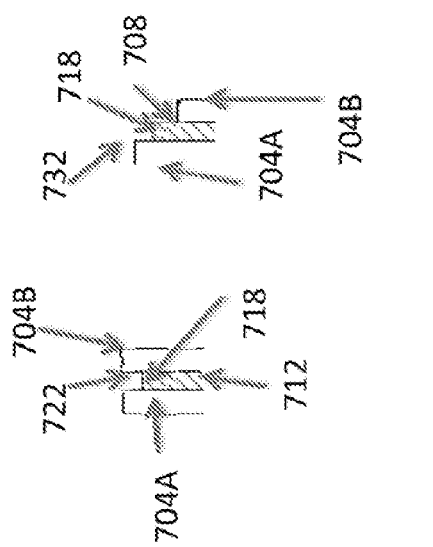
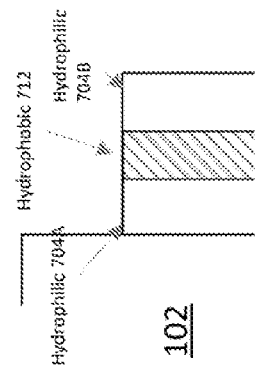
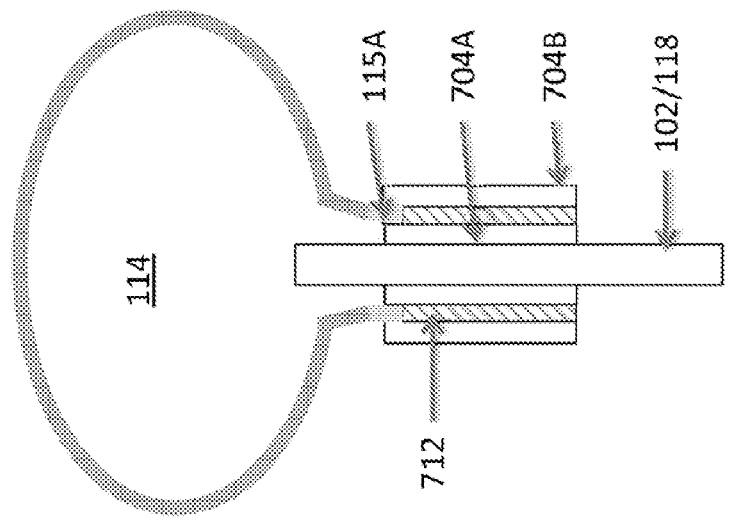
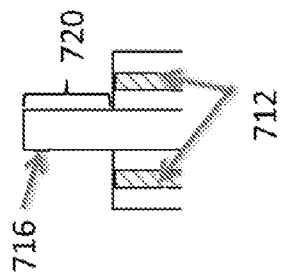

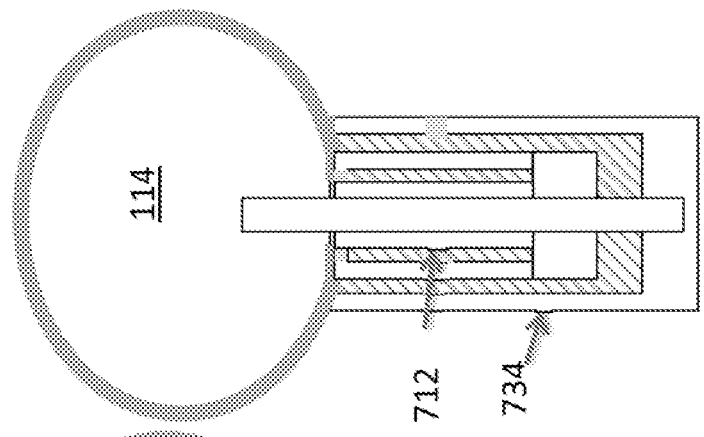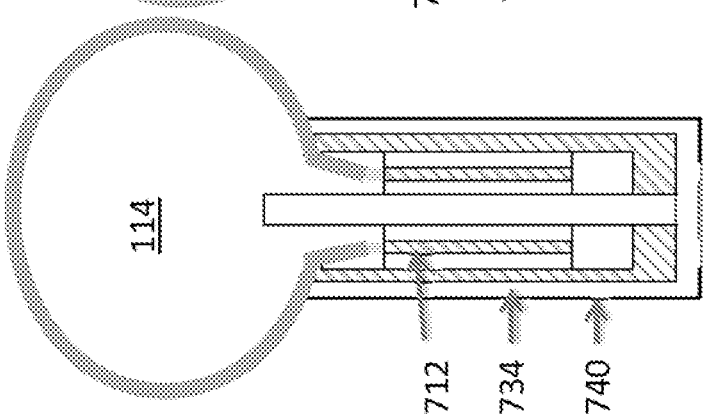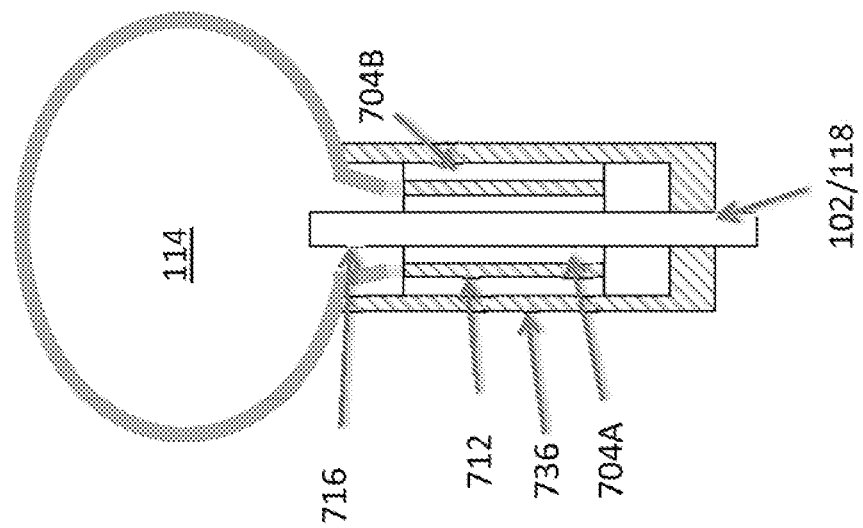

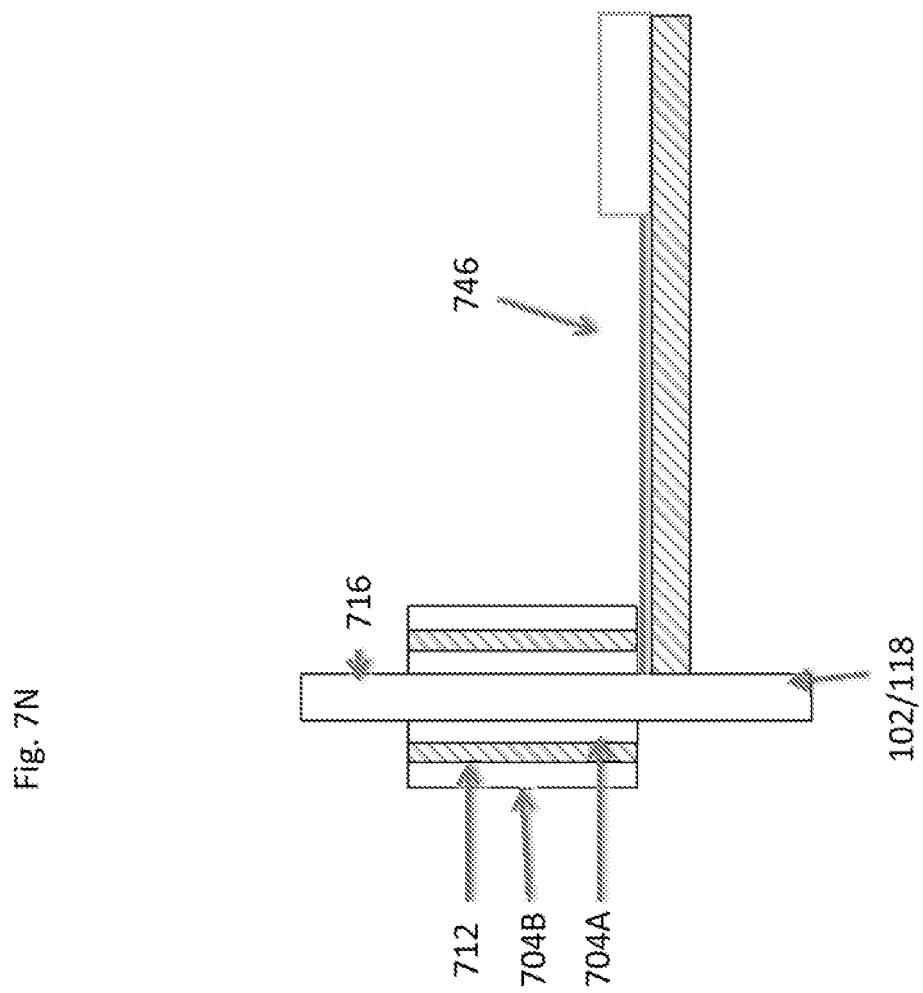

NANOWIRE-BASED DEVICES FOR LIGHT-INDUCED AND ELECTRICAL STIMULATION OF BIOLOGICAL CELLS

The present application claims benefit of priority of U.S. provisional patent application Ser. No. 61/565,041 filed on Nov. 30, 2011, which is incorporated herein by reference in its entirety.

FIELD

The present invention is directed to nanowire devices and methods of stimulating biological cells with photovoltaic devices.

BACKGROUND

Differences in the electrical charge across the membrane of neuronal cells provide one of the bases for communication between individual neurons in a network. In a normal biological system, these differences are achieved by passive and dynamic process involving, among others, ion channels and pumps that ensure an uneven distribution of negatively and positively charged ions (mainly sodium ($Na^+$), potassium ($K^+$), chloride ($Cl^-$), and calcium ($Ca2^+$)) on each side of the membrane, such that the cell is said to be polarized. The inside of the cell under resting conditions is more negative than the outside and changes in the movement of ions across the membrane render the cell even more negative (hyperpolarized) or less negative (depolarized). Changes in the movement of ions thus result in a change in the membrane potential of the neuronal cell and can be triggered, directly or indirectly, by e.g., the binding of ligands to specific membrane receptors, mechanical forces, temperature, or light.

A change of the membrane potential can also be achieved by a direct electrical stimulation of neurons, a technique which is widely used in neuroscience. Applications range from basic studies of biological neural networks to medical applications, such as deep brain stimulation or retinal implants.

The loss of specific neuronal cells in the brain leads not only to a loss of function but also to an imbalance in excitatory and inhibitory signals (which can involve several neuronal circuits) and are the cause of or contribute to the symptoms of several disabling neurological (e.g., Parkinson's Disease) and psychiatric disorders. Deep brain stimulation (DBS), also referred to as focal brain stimulation (FBS), is a form of electrotherapy used clinically to treat many of the symptoms observed in these diseases. It uses surgically implantable electrodes to stimulate a neuron or neural network in the brain through direct or indirect excitation of the cell membrane with an electric current or electric potential. The generated electrical impulses modulate neuronal activity, reducing some of the symptoms.

Visible electromagnetic radiation induces an activation of photosensitive proteins in specialized cells in the retina (rod and cone photoreceptors). The activation of these proteins leads to a change in the flow of ions across the photoreceptor cell membrane, which in turn determines the amount of neurotransmitter released by these cells. Genetic and acquired diseases, as well as trauma, can cause the death and loss of retinal photoreceptors leading to visual impairment and eventually complete blindness. Synthetic photosensors may be used to replace the function of defective biological rods and cones, providing light-induced electrical stimulation to the visual nervous system.

In a normal retina, the signals generated by the photoreceptors are passed on to bipolar cells and subsequently to retinal ganglion cells, which ultimately convey the visual information through the optic nerve to higher visual centers. Degenerative diseases and trauma can lead to a loss of axons in the optic nerve and loss of the ganglion cells, leading to severe visual impairment.

Neuroprotection refers to any strategy used to delay or prevent neuronal cell death. Depolarization of neuronal cells by e.g., increased extracellular $K^+$ or direct electrical stimulation have been shown to increase the survival of several neuronal cell types.

Conventional electrical stimulation devices use an external electric power supply to power the device. Even conventional artificial photosensitive cells, e.g., conventional retinal implants, use an external power supply to amplify the signal and/or make the device functional.

SUMMARY

One embodiment relates to a device including at least one photovoltaic cell and at least one nanowire configured to electrically stimulate a biological material in response to radiation.

Another embodiment relates to a neural probe device, comprising a semiconductor or conductor nanowire, and a hydrophobic edge seal located around a first portion of the nanowire. A protruding second portion of the nanowire is configured as an intracellular electrode.

Another embodiment relates to a method of stimulating biological material with a photovoltaic cell. The method comprises converting radiation to current or voltage with the photovoltaic cell, and providing current or voltage to the biological material using a nanowire to electrically stimulate the biological material.

BRIEF DESCRIPTION OF THE DRAWINGS

FIG. 2A longitudinal pn, FIG. 2B longitudinal pin, FIG. 2C core-shell pn and FIG. 2D core-shell pin.

FIG. 5 is a schematic illustration of a method of transferring nanowires from a growth substrate to a handle substrate.

FIG. 6 is a schematic front view of a retina with nanowire photovoltaic cell implants.

FIGS. 7A to 7N are schematic illustrations of a seal for sealing the nanowire inserted in an intracellular configuration into a cell.

DETAILED DESCRIPTION

Figure 1:
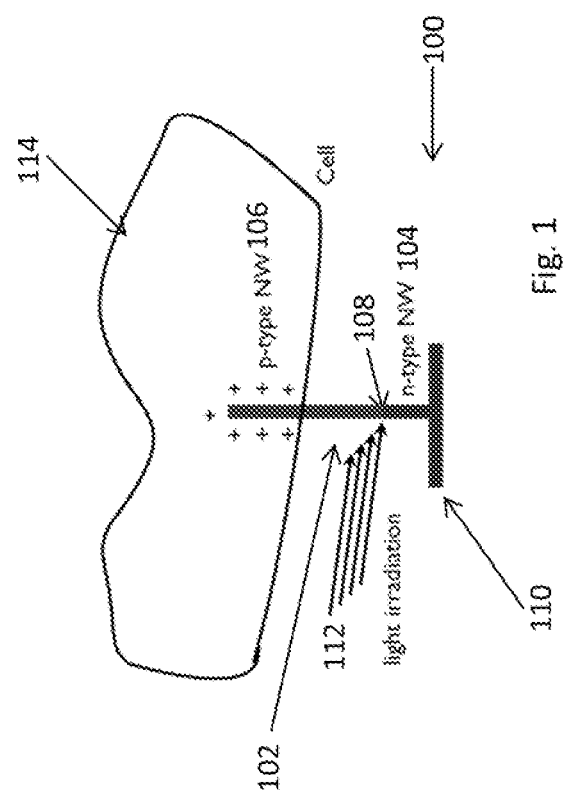
FIG. 1 is a schematic illustration of a device with at least one nanowire photovoltaic cell configured to stimulate a biological material according to an embodiment.

Conventional electrical stimulation devices use an external electric power supply. In contrast, photovoltaic devices convert incident radiation to electrical current and voltage which may be used, for instance, to directly stimulate the biological cell or alternatively to power other devices for cell stimulation. Furthermore, conventional, non-intimate, stimulation of cells comprises high current on the order of 10-100 µA for stimulation of the cells. Such excessive currents tend to affect large regions of cells and may also affect the cells in a degradable fashion.

By localizing the stimulating signal to one cell and creating an intimate contact to the cell, the power needed for stimulation can be decreased, by the way of direct stimulation of a single cell or even limited region of the single biological cell. This corresponds to a decreased amount of light intensity in the case where the stimulation of the cells is powered by a photovoltaic device.

One embodiment of this invention describes such an intimate nanowire biological cell contact, designed for low power use by improving resistance, leakage and capacitance of the contact. The contact provides a low power biological cell—nanowire electrical interface, reducing, minimizing or eliminating the need for external power of such applications.

Another embodiment relates to at least one radially insulated nanowire for intracellular insertion into a biological cell configured to electrically stimulate the biological cell, where the nanowire has a high resistance hydrophobic seal connected to the cell membrane. The seal is exposed in the radial insulating material substantially in a plane perpendicular to the axis of the nanowire. This configuration assists in providing an intimate contact between the nanowire and the interior of the cell with at least one GigaOhm resistance seal between the radial nanowire insulation and the cell membrane. The nanowire may be a photovoltaic nanowire that lacks an external power source or which has an external power source, and/or a non-photovoltaic nanowire which has an external photovoltaic or non-photovoltaic power source.

In one embodiment, the device is used for Deep Brain Stimulation (DBS). In this embodiment, a small diameter optical fiber is inserted in the brain in order to excite the nanowire photovoltaic cells, which will then very locally stimulate the neurons around the nanowires.

In another embodiment, the device is used in a retinal implant. The nanowire photovoltaic device is configured to convert incident radiation to electrical stimulation and provide the electrical stimulation to the visual nervous system. This approach could be called "synthetic optogenetics", by virtue of its use of synthetic devices (e.g., nanowire photovoltaic devices) instead of genetic modification to make cells sensitive to optical stimulation.

In yet another embodiment, the device is used as a neuroprotector. The nanowire photovoltaic cell(s) are used as a means of neuroprotection. They can provide light-induced electrical stimulation (and protection) to a biological material (e.g., retinal cells, brain cells, etc).

Thus, a photovoltaic based electrical stimulation device, which can be used for example for stimulating biological cells, could either power itself (i.e., an external power supply may be omitted) or require less power from an external source than a prior art device.

One advantage of some of the embodiments of the invention is that no external power supply is required, which significantly enhances the range of applications of the above described technique. For instance, retinal implants will no longer need to be connected by a wire to a power supply located on the outside of the eye, which will make retinal chips more sturdy and easier to use. For brain stimulation, stimuli to an implanted device may be transmitted wirelessly (using a light wavelength of sufficient transmittance in brain tissue) from a light emitting device, such as a UV, IR or visible radiation source, such as a lamp or laser located outside the brain tissue. Of course if desired, an optional external power supply (e.g., micro-battery, etc.) may be used in conjunction with the PV cells (e.g., to power the probes in a relatively dark environment).

Another advantage of the device is flexibility in circuitry. As noted above, the PV devices could be operated open circuit (no current flow due to the radial insulating layer with voltage stimulation only) or in current-drawing mode (using electric contacts, for example electrical contact(s) to one or both ends of the nanowire covered with a metal). Further light-powered circuitry could be included on-chip in the retinal implant chip, neuroprotection chip or DBS chip. It should be understood that voltage stimulation with insulating layer (capacitive contact) may be used instead of the current stimulation in any of the of contacts and configurations described herein. Thus, the electrode may be insulated from the biological material by an insulating layer to form a capacitive, contact in any of the embodiments described herein.

Another advantage of the nanowire device is biocompatibility and cell attachment. Neuronal cells can grow and thrive on substrates with vertical nanowires of a variety of semiconducting or metallic materials. The nanowires may provide good electric coupling. When neurons are cultured on nanowire containing substrates, vertical nanowires are known to interact very strongly with the cell walls, apparently without damaging them. Cells grown on nanowires, or with nanowires in solution, incorporate nanowires into their interior, or adhere strongly to the nanowire surface. This intimate contact can be expected to provide very good electric, coupling, minimizing the amount of electrical impulse (current or voltage) needed to trigger a neuronal cell response. The nanowires also provide good material flexibility and biocompatibility. Nanowire photovoltaic devices can be fabricated from a range of materials (e.g. Si, III-V or II-VI compounds, etc.) making it possible to choose materials for optical or electrical applications. In addition, the nanowire devices can be metalized or coated with other materials, such as different types of oxides, polymers, metal, etc., further raising the possibilities to optimize biostability, biocompatibility and electric coupling to cells by preventing their degradation in the biological medium and, for instance, helping to stimulate the biological material (e.g., insulating the conductive core from the environment biological medium, etc.) As such, the probes can be used for electrical stimulation of a biological material (in an extracellular or an intracellular configuration) and/or for detection of electrical signals from the biological material.

Suitable PV semiconductor nanowire materials include, but are not limited to, Si, Ge, SiGe alloys and III-V and II-VI compound semiconductors such as GaAs, InGaAs, InAlGaAs, CuInGaSe, InP, and GaN. In alternative embodiments, non-PV nanowire materials may include metals, such as Pt, Ti, Al, etc.

If desired, the outer surface of the semiconductor nanowires may be coated with an electrical conductor (e.g., metal, such as Au, Cu, etc.) to form an Ohmic contact, enabling the flow of electric current in the biological material. Alternatively, the semiconductor or conductor (e.g., metal) nanowire cores may be radially coated with an insulating layer shell, e.g., an atomic layer deposition (ALD) deposited oxide (e.g., silicon oxide), nitride (e.g., silicon nitride or oxynitride) or high-k dielectric material (e.g., aluminum oxide), for open circuit operation.

In preferred embodiments, the nanowire photovoltaic cells may be functionalized to be specifically bound to desired biological cells. The surface of the nanowires (and/or the surface of the insulating shell) is functionalized for promoting specific binding to a biological cell (by functionalizing the nanowires and/or the insulating shell with, for example, specific cell ligand). For example, the biological cell is a neuron. The nanowires may be functionalized for specific binding to other cells, such as brain cells, as desired. The biological cell may also be any retinal cell or a particular retinal cell type. Parts or the whole of the surface of the nanowire devices may be coated or may be functionalized by adequate chemical molecules (e.g., lipid bilayer, lipid monolayer, phospholipids, poly(ethylene glycol) ("PEG"), etc.) in order to facilitate overgrowth of cell tissue or penetration into the cell tissue. For instance, the upper part of the nanowire could be functionalized with molecules promoting cell adhesion, while the lower part could be coated or functionalized with molecules preventing cell adhesion (e.g., PEG, etc.).

Typical nanowire size ranges include a diameter (for cylindrical nanowires) or width (for nanowires having a polygonal cross section, such as GaN nanowires with a hexagonal cross section) of 5 to 500 nm, such as 10-50 nm, and a height or length (i.e., the axial dimension) of 0.05 to 10 µm, such as 0.5 to 5 microns. The nanowires described herein are also sometimes referred to as nanorods, nanocones, nanopyramids, nanowhiskers, nanoposts, nanotips, nanopillars, etc., depending on their shape.

There is in principle no lower limit on the density of the nanowires, they can be fabricated in sparse densities comparable to that of biological cells, therefore a configuration where one nanowire addresses on singular biological cells is possible if so desired. The density of the nanowires may be greater than 0.01 nanowire/square micron, such as greater than 0.1 nanowire/square micron, including greater than 1 nanowire/square micron. For example, the density of the nanowires may be greater than 5 nanowire/square micron, including greater than 10 nanowire/square micron, such as 50 to 1,000 including 50 to 100 nanowire/square micron.

Thus, the photovoltaic cells and structures based on individual nanowires can be fabricated with a density (e.g., tens of nanowires per square micron) that is very high compared to that of biological cells. Nanowire based devices can therefore address biological tissue with very high spatial resolution, and, if desired (for example to enhance signal or for color vision implants, or to improve the resolution of the vision with retinal implants), numerous nanowire photovoltaic structures can be used in order to address the same cell or its processes (dendrites or axon).

The nanowires can be organized in arrays, can be spatially arranged in lines, squares or different patterns and with different spacing. The photovoltaic cells that are located on or in a substrate can optionally be interconnected to each other in series and/or in parallel in order to provide a higher voltage or current to the device. Alternatively, there may be no electrical interconnection between the PV cells on the same substrate.

I. PV Nanowire Containing Device

A. PV Nanowires on Substrate

FIG. 1 illustrates an electrical stimulation device 100 according to an embodiment, where the device includes at least one nanowire photovoltaic cell 102 which is configured to electrically stimulate the biological material (e.g. specimen or an in vivo, living cell in a mammal) 114 in response to radiation. The nanowire photovoltaic cell may be used extracellularly or intracellularly, as will be described in more detail below.

In an embodiment, the nanowire photovoltaic cell 102 may comprise a single wire that has two portions of different conductivity types 104, 106, or two nanowires having different conductivity types. The first type may be n-type while the second type may be p-type or vice versa. The junction between the first and second portions or wires 104, 106 defines a pn junction 108. When radiation 112 of sufficient energy, i.e., greater than the bandgap of the semiconductor material comprising the nanowire, strikes the surface of the nanowire, the nanowire photovoltaic cell generates a direct current.

Figure 2:
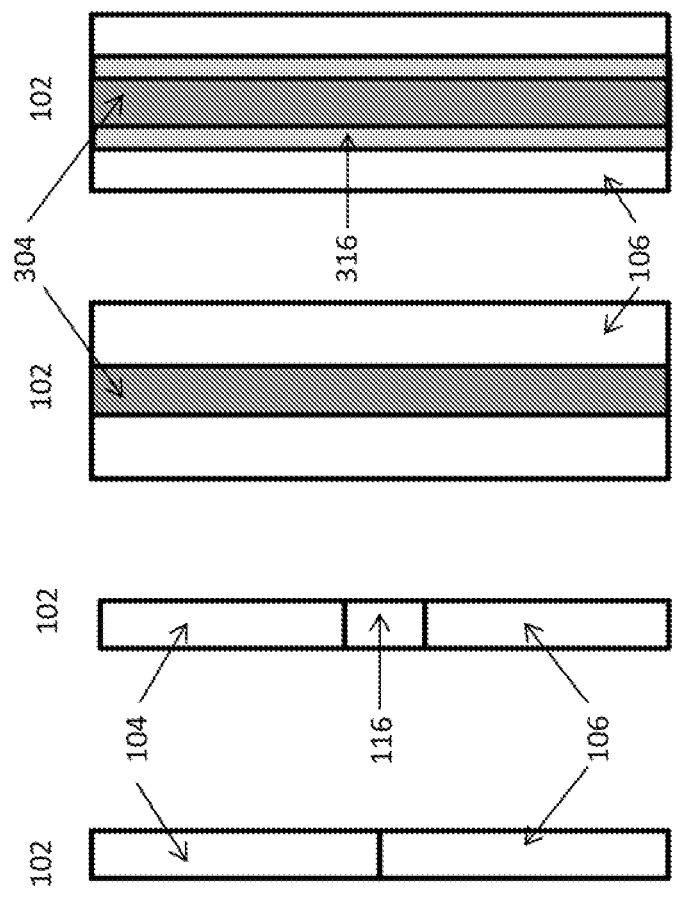
FIGS. 2A-2D are schematic illustrations of four configurations of photovoltaic nanowires that may be used with the embodiment illustrated in FIG. 1 including.

FIGS. 2A-D illustrate four different photovoltaic nanowire configurations that may be used with the electrical stimulation device 100 illustrated in FIG. 1. In the first configuration the nanowire photovoltaic device 102 is configured with a longitudinal configuration. As discussed above and illustrated in FIG. 2A, the nanowire photovoltaic cell 102 may comprise a single wire that has two portions of different conductivity types 104, 106 arranged end to end, or two nanowires having different conductivity types arranged end to end. The first type may be n-type while the second type may be p-type or vice versa. In the second configuration, illustrated in FIG. 2B, the nanowire photoelectric device 102 also has a longitudinal configuration. However, in this embodiment, an intrinsic region 116 is formed between the n-type region 104 and the p-type region 106. The intrinsic region 116 reduces undesired recombination at the pn (or np) junction, thereby improving efficiency of the nanowire photoelectric cell 102. In this configuration, the nanowire photoelectric device 102 is a p-i-n (or n-i-p) device. A third configuration is illustrated in FIG. 2C. In this embodiment, the nanowire photoelectric cell 102 has a coaxial or core-shell configuration. In this configuration, the core nanowire 304 has a first conductivity type while the shell 106 has a second conductivity type. Nanowire photoelectric cells 102 according to this configuration have a larger pn junction than comparably sized longitudinally configured nanowire photoelectric cells 102. The fourth configuration is illustrated in FIG. 2D. In this configuration, an intrinsic shell layer 316 is formed between the core nanowire and the shell. Thus, this device (similar to the device illustrated in FIG. 2B) is a p-i-n device. The nanowires described above may be coated by a thin layer (e.g., a radial shell) of one or more diverse materials (oxide, polymer, metal, etc.) preventing their degradation in the biological medium and, for instance, helping to stimulate the biological material (e.g., insulating the semiconductor nanowire core from the environment biological medium, etc).

In an embodiment illustrated in FIG. 1, the electrical stimulation device 100 includes a nanowire photovoltaic cell 102 that is located on a substrate 110. The nanowire photovoltaic cell(s) 102 is oriented substantially perpendicular, e.g., within 5 degrees, to the surface of the substrate. In alternative embodiments, the nanowires(s) is (are) oriented at a larger angle to the substrate surface, such as 5-45 degrees, such as 5-15 degrees.

B. Free Standing PV Nanowires

Figure 3:
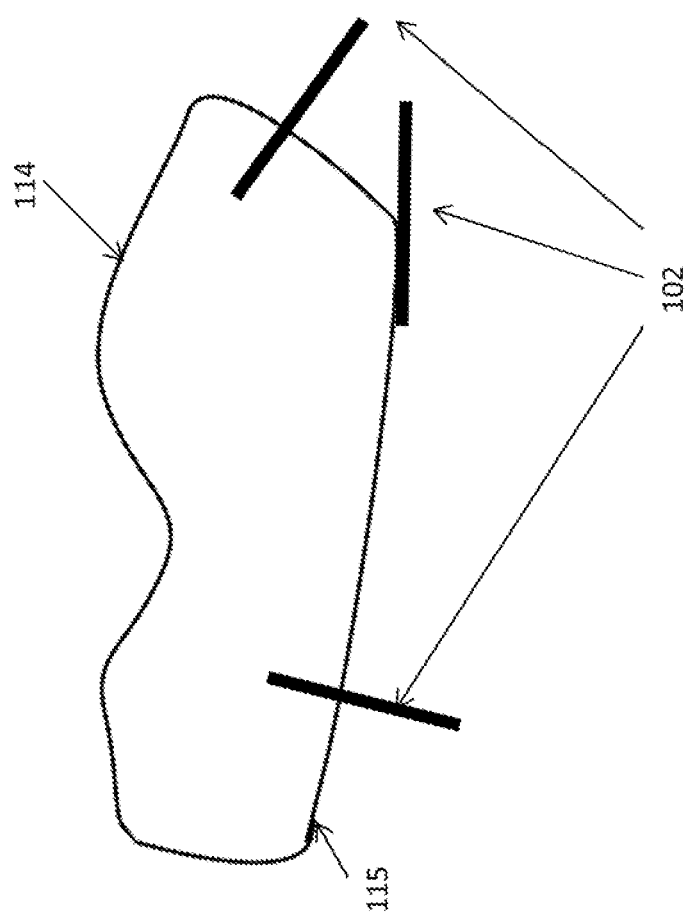
FIG. 3 is a schematic illustration of a substrate free nanowire photovoltaic cells configured to stimulate a biological material according to an embodiment.

In another embodiment, the electrical stimulation device 100 comprises a plurality of free standing nanowire photovoltaic cells 102, as shown in FIG. 3. That is, the nanowire photovoltaic cells 102 are not mounted on a substrate. The substrate 110 of the device 100 illustrated in FIG. 1 can be biodegradable and the nanowire photovoltaic cells 102 will be free standing after degradation of the substrate after the device 100 is placed in contact with the biological material (e.g., a biological cell) 114. Any suitable biodegradable material which is stiff enough to withstand tissue implantation may be used. Optionally, the biodegradable substrate can be loaded with anti-inflammatory drugs. The nanowires 102 are shown as extending through the cell 114 wall or membrane 115 in an intracellular configuration. As described earlier, PV devices could be operated open circuit (no current flow due to the radial insulating layer with voltage stimulation only using a capacitive contact) or in current-drawing mode (using electric contacts, for example electrical contact(s) to one or both ends of the nanowire covered with a metal). Alternatively, an extracellular configuration may be used, as will be described in more detail below. For retinal implants, the nanowire photovoltaic array will be placed intraocularly, subretinally (i.e., beneath the retina) or epiretinally (i.e., on the surface of the retina). A significant advantage of this embodiment is the absence of substrate in the long-term implant.

II. Nanowire Probes Powered by PV Cell

Another embodiment comprises at least one photovoltaic cell configured to provide electrical power to another device (e.g., non-PV electrical conductor (such as metal) or semiconductor nanowire) which in turn provides electrical stimulation in an extracellular or an intracellular configuration) to a biological material. The powered device could also be a probe detecting electrical signals from the biological material (e.g. neurons).

Figure 4:
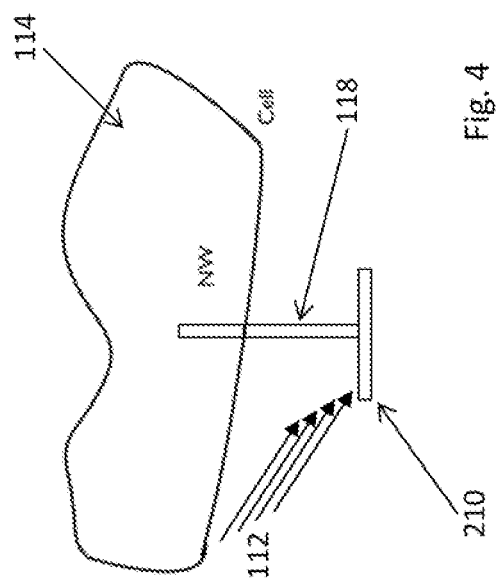
FIG. 4 is a schematic illustration of a nanowire probe device powered by least one photovoltaic cell configured to stimulate a biological material according to an embodiment.

FIG. 4 illustrates a device of this embodiment. In this embodiment, the substrate comprises a planar photovoltaic cell 210. The planar photovoltaic cell 210 may be an organic photovoltaic cell, a Graetzel photovoltaic cell, a p-i-n or p-n inorganic semiconductor photovoltaic cell or a Schottky junction cell. The nanowire (e.g., nanotip) probes 118 may be operatively connected to the photovoltaic planar photovoltaic cell 210. The probes 118 may be grown on the planar photovoltaic cell 210 or fabricated separately and connected over the surface of the planar photovoltaic cell 210. The probes 118 may be made of a doped semiconducting or conducting material (metal, electroconductive polymers, etc). Suitable materials include, but are not limited to, Si, Ge, SiGe alloys and III-V and II-VI compound semiconductors such as GaAs, InGaAs, InAlGaAs, CuInGaSe, InP, and GaN, or metals and metal alloys, such as Au, Cu, etc.

The probes 118 may be coated by a thin layer of diverse materials (oxide, polymers, metal, etc) preventing their degradation in the biological medium and, for instance, helping to stimulate the biological material (e.g., insulating the conductive core from the environment biological medium, etc). In this embodiment, the probes 118 rather than the PV nanowires 102 of the previous embodiment can be used for electrical stimulation of a biological material (in an extracellular or an intracellular configuration) and/or for detection of electrical signals from the biological material. Alternatively, the probes 118 may comprise semiconductor PV nanowires that are located on a planar PV cell substrate 210.

III. Method of Making the Device

The nanowires 102 or probes 118 may be grown on their respective substrate 110, 210 using any suitable method, such a vapor-liquid-solid (VLS) growth using metal catalyst nanoparticles described in U.S. Pat. No. 7,682,943 issued on Mar. 23, 2010 to Samuelson et al., or by a catalyst free, epitaxial CVD growth on portions of the substrate material exposed in nanoscale openings in an insulating mask described in U.S. Pat. No. 7,829,443 issued on Nov. 9, 2010 to Seifert, et. al., both of which patents are incorporated herein by reference in their entirety.

However, in another embodiment if the original growth substrate is not suitable for biological use, then the nanowires 102 or probes 118 may be transferred from the original growth substrate onto a desired biocompatible or biodegradable substrate. As illustrated in FIG. 5, it is possible transfer the nanowire photovoltaic cell(s) 102 from their original substrate growth substrate 110 onto (or into) a biodegradable or a biocompatible/non-degradable flexible material substrate or matrix 510 (e.g., polymer, Gelatin, Poly-CaproLactone, Hyaluronic acid, etc.). The transfer can be realized, for example, by embedding the nanowires 102 on the growth substrate 110 in the material of the carrier substrate 510 (e.g., by forming the carrier substrate 510 around the tips of the nanowires 102 or by insertion of the nanowire(s) in the carrier substrate 510 material while it is soft or liquid and then solidifying the carrier substrate 510 material). The embedding step is followed by removing the growth substrate 110 by selective etching or by using a selectively removable release layer between the substrate 110 and nanowires 102, etc. to leave the nanowires 102 on the carrier substrate 510. Alternatively, the transfer may be realized by providing an adhesive layer on the surface of the carrier substrate 510, adhering the nanowire 102 tips to the adhesive layer and removing the growth substrate 110 by selective etching, release layer use or by mechanical pulling force. The seals 702 around the nanowires 102 are also shown in FIG. 5 and will be described in more detail below with respect to the subsequent Figures.

In another embodiment, rather than growing the nanowires 102 or probes 118 on a substrate 110, the nanowires may be grown in the vapor phase from metal catalyst particles in a vapor stream by an Aerotaxy method described in PCT published application WO 2011/142717 A1 published on Nov. 17, 2011 and naming Samuelson et al. as inventors, and its U.S. national stage application Ser. No. 13/696,611, both of which are incorporated herein by reference in its entirety. In the Aerotaxy process, nanometer size catalyst particles are aerosolized and provided to a growth chamber. Vapor phase semiconductor constituents are then supplied to the growth chamber. Nanowires 102 grow from the catalyst particles via the vapor-liquid-solid (VLS) process. Doping of the nanowire is accomplished by adding a dopant containing vapor to the growth atmosphere. The input gases and growth conditions (temperature, pressure) are may be changed during growth of the nanowire to form a radial shell around the nanowire core to form a pn or pin junction nanowire PV cell 102. Alternatively, non-PV probes 118 may be formed instead.

The nanowire PV cells 102 are collected and provided to an alignment chamber having the carrier substrate 510. The nanowires may be placed on the substrate using an ink jet process, a stamping process or aerosol spray process. The alignment chamber includes two electrodes, one located behind (under) the substrate and the other is located above the substrate. The nanowires on the substrate are exposed to radiation (UV, visible or IR) and a voltage is applied across the electrodes which generates an electric field that induces a dipole in the nanowires. The nanowires 102 rotate to align the dipoles in the electric field, thereby orienting the nanowires 102 in a controlled fashion to stand up vertically (e.g., on one tip) on the carrier substrate 510, as described in PCT published application WO 2011/078780 published on Jun. 30, 2011 naming Samuelson, et al. as inventors and its U.S. national stage application Ser. No. 13/518,259, both of which are incorporated herein by reference in their entirety.

In an embodiment, the device 100 includes one or a plurality of nanowires 102 on a substrate 110, 210, 510, which can be biodegradable, or non-biodegradable but biocompatible, flexible and as large as possible, or non-biodegradable but biocompatible and small. If the substrate is flexible, the nanowire(s) 102 or probes 118 may be mounted on the flexible substrate or comprised in a flexible membrane. This flexible substrate will facilitate incorporation in biological tissue, but will be stiff enough to withstand tissue implantation. If the substrate is biodegradable, the nanowire photovoltaic cells 102 may be free standing after degradation of the substrate.

In an embodiment, the planar photovoltaic cell substrate 210 may be, for example, a substrate that is biocompatible, partly non-biodegradable and flexible, or biocompatible, partly non-biodegradable and small. The PV part of the substrate may be coated in radiation transparent, biocompatible, non-biodegradable material, while the portion of the substrate supporting the PV part of the substrate may be biodegradable and large or non-flexible and will degrade after being placed in contact with the biological material.

IV. Methods of Using the Device

Embodiments of the invention include methods of stimulating biological cells 114 with an electrical stimulation device 100. In an embodiment, the method includes converting radiation 112 to current or voltage with nanowire photovoltaic cells 102 or planar photoelectric cells 210. The method also includes providing the current or voltage to the biological cell 114 to electrically stimulate the biological cell 114. In performing the method, the nanowire photovoltaic cells 102 or the probes 118 may be inserted (intracellular) into the biological material (e.g., a biological cell, such as a retinal cell) 114 or provided adjacent (extracellular) to the biological material (e.g., cell 114) to generate a voltage or current in the biological material.

A. Retinal Implant

An embodiment includes using the electrical stimulation device 100 as a retinal implant. In this embodiment, the retinal implant comprises nanowire photovoltaic device 102 configured to convert incident radiation to electrical stimulation and provide the electrical stimulation to retinal cells.

The nanowire photovoltaic cells 102 (on a substrate 110 or 510 as shown in FIGS. 1 and 5 or substrate free as shown in FIG. 4) are placed intraocularly, in a sub- or epiretinal position, in subjects lacking most or all photoreceptor cells to replace the function of the lost cells. If a substrate 110 or 510 is used epiretinally, then it should be transparent to visible radiation.

For example, the implant may be located epiretinally with the nanowire photovoltaic cells 102 facing the inner retinal surface in order to provide electrical stimulation to retinal ganglion cells. A differential stimulation of ON and OFF ganglion cells may be achieved by combining in the array both photosensitive and insensitive nanowires in a pattern that, for example, would resemble the spatial distribution of these cells in the ganglion cell mosaic.

One embodiment of the retinal implant comprises of at least one first array of photovoltaic nanowire devices absorbing light of a first peak wavelength and of at least one second array of photovoltaic nanowire devices absorbing light of a second peak wavelength. The array forms patterns resembling the biological distribution of color sensitive cones or of cones and rods in the retina. The plurality of nanowire photovoltaic cells 102 can have different bandgaps (e.g., by using different materials) to absorb radiation having different ranges of wavelengths or different peak wavelengths, corresponding to one or more of IR, UV, visible light or subranges of visible light (e.g., colors red, green, blue, cyan, yellow, magenta, orange, indigo and/or violet). For instance, a retinal implant employing photovoltaic cells that have the same spectral sensitivity as cone photoreceptors (which respond specifically to different wavelengths), and forming patterns resembling the biological distribution of cones, may provide color vision to a mammal, such as a human.

The materials of the nanowire photovoltaic cells 102 and the planar photovoltaic cells 210 may be selected based on the expected incident radiation. The radiation may be, for example, solar. However, when inside a building, especially in an internal office or laboratory, or outside at night, the radiation may be from a lamp. Depending on the lamp, this radiation may be ultraviolet (UV), visible, infrared (IR) or a combination thereof.

One embodiment of the retinal implant comprises at least one array of photovoltaic nanowire devices and at least one wavelength selective filter situated in the light path. The filter(s) may form patterns. For example, if the nanowire photovoltaic cells are placed in the subretinal space with the aim of replacing the function of the lost photoreceptor cells, the filters may form patterns, resembling biological distribution of the cones. Lower-bandgap photovoltaic cells 102 (e.g., PV nanowires) may be equipped with optical band pass filters to block out high-frequency radiation, in order to be selective to low-frequency radiation. The bandpass filter may filter out light above IR in order to make an IR sensitive implant. The filter may be located in the path of the radiation from the iris to those PV nanowires 102 which are located in the area of the retina (e.g., the parafovea region or belt) which contains rods which are responsive to dim light and are responsible for night or low light vision.

Alternatively, as shown in FIG. 6, narrow bandgap semiconductor PV nanowires (e.g., InAs, etc.) having a bandgap below the visible light range (e.g., below 1.24 eV which corresponds to a wavelength of greater than 700 nm) may be located in the region of the retina 600 (e.g., in the parafovea belt 606 surrounding the fovea 604 and foveola 602) which contains rods which are responsive to dim light and are responsible for night or low light vision. The location of the optic disc 608 is also shown in the Figure. Wider bandgap semiconductor PV nanowires (e.g., GaAs, GaN, etc.) may be located in the regions of the retina 600 which contain cones which are responsible for day time vision (e.g., the foveola region and/or the fovea region 604).

Thus, by choosing the bandgap of the nanowire material, and/or by combining the photovoltaic structure with an optical filter, for example a shell made of a semiconductor material with a different bandgap, the light sensitivity can be limited to a defined (narrow or wide) range of light wavelengths.

In an embodiment, the nanowire photovoltaic cells 102 are located on a substrate 110 in a specific pattern. In the human eye, photoreceptors are not distributed homogeneously similar to a CCD device, but follow a specific geometry. In addition, the cone photoreceptors are highly concentrated in the fovea which provides sharp vision in a limited part of the field of vision. Most likely, the way information is collected by the eye and processed by the retina and brain is adjusted to the retinal structure. Given the high density with which nanowire photovoltaic devices can be placed on a substrate, and the ability to predetermine the position of each device (e.g., in arrays of nanowire photovoltaic absorbing light of different wavelength as described above), it would be possible to mimic the natural structure of the retina for better compatibility with human vision (for example the way information is processed by retina and brain).

B. DBS

In another embodiment, the nanowire photovoltaic device 100 is delivered to the brain subthalamic nucleus (or related brain areas used for DBS) for Deep Brain Stimulation (DBS). The nanowires 102 can be coated with Poly-ethylene glycol (PEG) or similar biocompatible polymer to avoid detection by the immune system. An optical fiber is inserted in the brain in order to excite the PV nanowires using a radiation source (e.g., UV, VIS or IR lamp or laser). The radiation is then transmitted through the optical fiber to the PV nanowires 102 which then generate a local current to very locally stimulate the neurons around the nanowires.

The main advantages of this method are (i) the small diameter optical fiber inserted in the brain (tens of microns, e.g., 10-100 microns, in diameter) compared to the current DBS electrode (millimeters in diameter), which would result in less tissue inflammation and (ii) more focal stimulation of the brain, due to the small size of the nanowires, compared to the prior art DBS electrodes.

C. Neuroprotector

As discussed above, electrical stimulation promotes the survival of numerous cell types. In an embodiment, nanowire photovoltaic cells 102 are used as a neuroprotector. This can provide light-induced electrical stimulation (and protection) to a biological material (e.g., retinal cells, brain cells, etc). For instance, in Retinitis Pigmentosa, mutations in mostly rod-specific genes are responsible for the demise of these cells. Yet, over time, a loss of cone photoreceptors is also observed, which ultimately can lead to complete blindness. This has led to the assumption that delaying or preventing rod cell death may help preserve cone cells. The photovoltaic cells 102 are located on a substrate 110 and are placed subretinally, with the nanowires facing the inner retina. The device is implanted at a relatively early stage of the Retinitis Pigmentosa disease in the parafoveal region 606, as illustrated in the FIG. 6, where the highest density of rods occurs. This will provide light-induced electrical stimulation (and protection) to the rod cells, preserving in this manner the cone photoreceptor cells.

In glaucoma, there is a progressive loss of retinal ganglion cells, which can eventually result in complete blindness. In an embodiment, neuroprotection of ganglion cells is achieved by employing nanowire photovoltaic cells 102 located on a transparent substrate 110 (or free standing cells 102), which is placed epiretinally (on the retina surface with the nanowire photovoltaic cells facing the inner retinal surface) in order to provide electrical stimulation to the retinal ganglion cells to decrease or avoid the onset of glaucoma.

D. Incident Radiation Control

The wavelength of the radiation (e.g., visible light) incident on PV cells 102, 210 can also be selected or controlled to increase its penetration depth in biological material 114. Thus, the peak wavelength or wavelength range of the radiation emitted by the radiation source (e.g., lamp or laser) is selected to correspond to the wavelength or wavelength range of maximum transmission through the biological material 114 of interest (e.g., eye material or brain material). The radiation may also be directed to the site of the photovoltaic nanowire(s) 102 by an optical fiber as described above.

The radiation source can be connected to control electronics that may include a electrical sensor (e.g., current or voltage sensor) and/or a radiation sensor. The sensors may monitor the incident radiation and/or optical or electrical output from the biological material 114. The control electronics adjust the incident radiation characteristic(s) from the radiation source based on the data obtained by the sensor(s). The characteristic(s) may include radiation intensity, peak wavelength, output wavelength range, pulse duration (for pulsed radiation), pulse frequency, etc. Thus, the radiation source may be adjusted based sensory or input data or according to a predetermined or programmable sequence.

In an embodiment, the nanowires serve as connection between an electrical circuitry and biological cells. The electrical circuitry may be externally powered or a light-powered circuitry (e.g., nanoelectronic circuit, etc). The circuit can aid in controlling or transforming the photovoltaic response such that they stimulate the cells according to a specific time resolved pattern. For example, the pattern would help to generate images with a higher spatial or temporal resolution. The response pattern could resemble, for instance, the firing code of ganglion cells. Also, a differential stimulation of ON and OFF ganglion cells may be achieved by triggering a different response of nanowires according to a pattern that resembles to the spatial distribution of these cells in the ganglion cell mosaic, as described above.

In an embodiment, for optimal cell stimulation and to avoid tissue damage, the incoming light to the photovoltaic cell(s) can be phased with different pulse duration and period. In the case of a retinal implant, this can be realized, for instance, with dynamic filters placed outside of the eye to transform continuous incident radiation from a light source located outside the eye into pulsed radiation. The incoming light to the photovoltaic cell(s) can be phased with different pulse duration and period by using a digital light projector, encoding the visual information (see S. Nirenberg et al., PNAS, Sep. 11, 2012, vol. 109, no. 37, pages 15012-15017, incorporated herein by reference in its entirety), or by using a stimulus system or method, similar to the one used in a multifocal electroretinogram, that would deliver stimulation to the retinal cells in a defined temporal and spatial pattern to encode the visual information, or by using (an) optical fiber(s). The pattern stimulation could mimic, for instance, the firing code of ganglion cells. The pulse duration and period can be modified depending on the intensity of the incoming light. The photovoltaic cells in the eye will transform the pulsed light signal to electrical stimulation to the retinal cells. This procedure would also allow for amplification of the signal. The momentary light pulses, mimicking nerve pattern signals, may be appreciably stronger than the ambient light, enabling retinal photovoltaic cells to respond easily without external power.

V. Seal for Intracellular Use

A. Band Seal

Embodiments of the invention include nanowire PV cells 102 or nanowire probes 118 which may be located in an intracellular configuration (the nanowire is going through the cell 114 membrane 115). Furthermore, the substrate containing or substrate-free nanowire photovoltaic cells 102 or probes 118 may be inserted into the biological cells 114 in a self-organized (i.e., self-assembled) manner. For example, as shown in FIGS. 7A-7C a portion (e.g., middle portion located between end portions) of the nanowire 102 or probe 118 may be functionalized with a radial band or belt of hydrophobic material 702, which will be referred to as a seal herein. The nanowire 102 or probe 118 is then likely to position the seal 702 portion into the cell 114 membrane 115 in a self-organized fashion, such that an end part of the nanowire 102 (e.g., p-doped portion 106 or n-doped portion 104) or the probe 118 is inserted into the cell 114.

FIG. 7A illustrates an embodiment where a seal 702 comprising a 5-10 nm wide band of hydrophobic molecules (e.g., carbonated molecules, fluorinated molecules, silanes, thiols, an inorganic thin layer, such as a hydrophobic metal, etc.) is patterned to be located around the nanowire 102. For example, the seal 702 is located around the intrinsic portion 116 of the nanowire PV cell 102, providing a GigaOhm or greater (e.g., 1 to 5 GΩ) resistance seal ("GigaOhm seal") between the cell membrane 115 and the nanowire 102 or probe 118. Such gold or nickel seals around metal post shaped probes are described in Verma P, Melosh NA. Gigaohm resistance membrane seals with stealth probe electrodes, Applied Physics Letters, 97(3), 033704 (2010) and US published application 2012/0222970 A1, both of which are incorporated herein by reference in their entirety. According to the Verma et al., article, a metallic post electrode with a hydrophobic band that mimics transmembrane proteins drives insertion into the lipid membrane and forming a tight seal at the electrode-membrane interface. Verma et al. demonstrated spontaneous gigaohm seals with an average seal resistance of 3.8±1.9 GΩ using red blood cells, and showed the nanoband is the key attribute for high resistances.

A single cell still represents an appreciable capacitive load needing signal power to be overcome in order to activate a biological function. By decreasing the electrode size, the interface area and electrical path in the cell/nanowire contact, the capacitive contribution of mainly the cell 114 membrane 115 will be minimized and thereby appreciably decrease the level of electrical stimulation needed to activate a biological reaction.

The nanowire 102 or 118 and the cell 114 preferentially form a singular insulated system. Insulation is an important leakage inhibitor, not only for limiting power need but also in order to inhibit crosstalk between different nanowire cell systems. In many of the figures a common electrode from the nanowire outer part, directly or indirectly connected to the saline solution, is assumed. In some embodiments each device comprises an individual outer electrode in close contact to the membrane.

In order to achieve an ultra low power cell-nanowire connection, achieving low capacitance and leakage is desirable, while internal resistance of the probing nanowire should be low. As shown in FIG. 7B, a radial insulating material layer or shell 704 around the nanowire 102/118 that protrudes outside the membrane 115 will decrease or prevent leakage paths to the saline bodily solution. The insulating layer shell 704 may be an atomic layer deposition (ALD) deposited oxide (e.g., silicon oxide), high-k dielectric material (e.g., aluminum oxide) or nitride (e.g., silicon nitride or oxynitride) deposited by a variety of techniques.

The shell 704 preferably covers the portion of the semiconductor or metal nanowire 102/118 core that is located below the seal 702 and extends outside the cell 114 membrane 115, as shown in FIG. 7B. Thus, the insulating material is extended from the cell membrane 115 by the GigaOhm seal 702 to the insulating shell 704. The membrane 115 of the cell 114 forms an insulating entity with the insulating shell 704, and the two ends 104, 106 of the nanowire 102 are situated on opposite sides (i.e., outside and inside of the cell membrane 115, respectively) of the insulating entity. Thus, as shown in FIG. 7B, the seal 702 is positioned in contact with the insulating shell 704 in order to form a continuous insulating entity comprising the membrane 115 contacting the seal 702 and the radial insulating shell 704.

If desired, plural insulating shells may be formed around the nanowire 102/118. For example, as shown in FIG. 7C, the inner insulating shell 704A radially surrounds the nanowire 102 core. A semiconductor or metal shell 706 radially surrounds the inner insulating shell 704A. An outer insulating shell 704B radially surrounds the shell 706.

B. Edge Seal

For a GigaOhm seal 702 to form the hydrophobic surface, the band seal 702 should narrow, e.g., 5-10 nm in width. Such seals 702 are conveniently formed using a 5-10 nm thick Au or Ni layer around the nanowire. However, it may be difficult to precisely form a 5-10 nm thick band around the middle of the nanowire such that the entire 5-10 nm high or thick radial surface 708 of the band seal 702 is exposed for contacting the inside (i.e., inner edge 115A) of the membrane 115, as shown in FIG. 7D. Furthermore, the metal band seal 702 shown in FIGS. 7A and 7D may also be a leakage path.

Thus, in another embodiment, an edge seal 712 shown in FIGS. 7E-7N is used instead of or in addition to the band seal 702. The edge seal 712 offers a higher precision of the thickness of the seal and a higher certainty of insulation between the nanowire 102/118 and the membrane 115.

The edge seal 712 comprises a hydrophobic material (e.g., a metal such as Au or Ni) having an edge surface 718 (rather than an entire radial surface 708 of the band 702) exposed for contacting the inside (i.e., inner edge 115A) of the membrane 115. The edge surface 718 is a surface that is substantially perpendicular to the longitudinal axis 714 of the nanowire 102/118. As used herein, substantially perpendicular means within 0-25 degrees, such as 0-10 degrees from perpendicular. In contrast, the radial surface 708 of the edge seal 712 is substantially parallel to the axis 714. In other words, the hydrophobic ring seal 712 is formed in a lateral or horizontal plane. As shown in FIG. 7E, in one non-limiting configuration, it is believed that the membrane 115 will curve down to the edge seal 712, such that the inner edge 115A of the membrane 115 contacts and seals against the exposed edge surface 718 of the seal.

As shown in FIGS. 7E and 7F, the edge seal 712 may comprise a hydrophobic shell (e.g., a metal shell) surrounding the nanowire 102/118. Preferably, the radial thickness of the edge seal 712 in a direction perpendicular to axis 714 is 5 to 10 nm. This means that the width of exposed edge surface 718 of the edge seal 712 is also 5 to 10 nm. If desired, the edge seal 712 may be physically separated from the nanowire 102/118 by an insulating shell 704A.

Preferably, at least 50%, such as 75-100% of the outer radial surface 708 of the edge seal 712 is covered by a radial insulating shell, such as shell 704B shown in FIG. 7E. Preferably, the insulating shells 704A, 704B are hydrophilic while the seal 712 is hydrophobic, as shown in FIG. 7G. The seal 712 is exposed in the radial insulating material 704A, 704B substantially in a plane perpendicular to the 714 axis of the nanowire.

Since the radial surface 708 of the edge seal 712 is covered by the insulating shell, the axial thickness of the seal 712 (i.e., height of the radial surface 708 parallel to axis 714) may be greater than 10 nm, such as 25 nm to 5 microns, for example 100 nm to 3 microns. Thus, less precision is needed to form the edge seal 712 than the band seal 702 because the radial thickness of the seal 712 is easier to control by shell deposition thickness than the axial thickness and there is no requirement to precisely pattern the seal to achieve a 5-10 nm axial thickness.

The edge seal 712 may be limited in vertical (i.e., axial) direction if desired to avoid leakage to the lower protrusion of the nanowire or, if the seal 712 material is opaque, to enhance transparency of the radial layers. For example, the edge seal 712 may have a shorter axial height or thickness than the axial height or thickness of the insulating shells 704A, 704B, as shown in FIG. 7E. Alternatively, the edge seal 712 may have the same axial height or thickness as the axial height or thickness of the insulating shells 704A, 704B to simplify fabrication of the device.

Sequential radial layers (i.e., shells) 704A, 704B, 712 may be formed on the nanowire using any suitable methods which can form layers with high thickness accuracy, exemplified but not limited to ALD, sputtering or evaporation methods. As shown in FIGS. 7E and 7F, the height 720 of the intracellular part 716 of the nanowire 102/118 may be set by a precise down-etch (e.g., selective etch) of the shells 704A, 704B, 712. Thus, the axial length of the nanowire which penetrates into the cell 114 through the membrane 115 is predetermined by the length or height 720 of the intracellular part 716 of the nanowire 102/118 which extends from the tip of the nanowire to the edge surface 718 or the top of the shell(s).

The intracellular part 716 of the nanowire may be considered a top electrode part which extends a predetermined height 720 above the insulating shell(s) 704A, 704B and the edge seal 712 shell positioned in proximity to the top electrode. Depending on the strength of ionic screening in the solutions in and outside the cell this height 720 is expected to have direct influence on the electrically affected area of the membrane 115 and the number of ionic channels to be excited. The effective size of the cell/nanowire interface will affect contact leakage and capacitance to resistance ratio. To take full advantage of ionic screening the opposing electrodes should optimally be small and positioned in close proximity on each side of the membrane. Lowering the height 720 will localize the contact, involve a smaller area of the cell membrane 115 and thereby lower the device power requirement.

In one embodiment, the edge surface 718 of the edge seal 712 is recessed compared to at least one of the hydrophilic insulating shell(s) 704A, 704B, as shown in FIGS. 7H, 7I and 7J. For example, as shown in FIGS. 7H and 7I, the edge surface 718 is recessed between both hydrophilic insulating shell(s) 704A, 704B to form a ring shaped contact trench 722 in which the inner edge 115A of the membrane 115 contacts the edge surface 718. Since the edge 115A of the membrane is wedged into the trench 722 between two insulating shells, the contact resistance is increased and leakage is decreased. The recessed edge surface 718 forming the contact region 722 may be formed by selective etching of the seal material compared to the insulating shell material.

In another embodiment shown in FIG. 7J, the edge surface 718 is recessed below the inner hydrophilic insulating shell 704A to form a ring shaped step contact region 732. However, the outer shell 704B is recessed below the edge surface 718 of the edge seal 712 to form an outer ring shaped step. Thus, the contact region 732 contains both the exposed edge surface 718 and an upper portion of the radial surface 708 of the edge seal 712. At least 50%, such as 75-100% of the radial surface 708 of the edge seal 712 is covered by a radial insulating shell 704B and less than 50% of the radial surface 708 is exposed in the contact region 732 for contact with the inner edge 115A of the membrane 115. The recessed edge surface 718 forming the contact region 732 may be formed by selective etching of the seal 712 material compared to the inner insulating shell 704A material and by selective etching of the outer insulating shell material 704B compared to the inner insulating shell 704A material and the seal 712 material. In this embodiment, the inner and outer insulating shell materials may be different from each other (e.g., silicon nitride and silicon oxide, etc.) to allow the selective etching.

The nanowire 102/118 may include one or many a radial shell layers, as shown in FIGS. 7K, 7L and 7M. The device may include the intracellular part 716 of the nanowire which may be considered a top or inner electrode part of the device, as discussed above. The device may further include a second electrode 736. The second electrode 736 may be a radial shell made of metal or another conductive material which extends around the outer insulating material shell 704B, as shown in FIG. 7K.

Since the second electrode 736 may be exposed to the saline environment or making close contact to the membrane 115 (i.e., in form of a radial electrode or an electrode along one side of the nanowire), preferably another outer insulating shell 734 and/or an outer biocompatible barrier shell 740 are located around the second electrode and insulates the device from the saline environment, as shown in FIGS. 7L and 7M.

If the nanowires 102 are photovoltaic or have light detecting diode functionality, then the shell layers 704A, 704B, 712, 736 and 740 are preferably transparent to the radiation used by the device (e.g., IR, UV and/or VIS). The hydrophobic edge seal 712 is preferably situated on at least the inner insulating shell 704A which forms a single insulating entity with the membrane. As noted above, inner electrode part 716 can be designed to penetrate from a few nanometers to several microns through the membrane 715 into the cell 714. The outer electrode 736 is connected to the other side of the p-i-n or pn junction of the nanowire PV cell 102. For a fully intimate, low power contact, the distance between the inner electrode (e.g., nanowire 102 portion 716) and the second electrode 736 may be less than 500 nm, such as less than 200 nm, such as less than 100 nm, such as less than 10 nm, for example 5-9 nm.

In another configuration illustrated in FIG. 7N, the second electrode 746 comprises an external electrode which contacts the lower part of the nanowire 102/118 below the seal 712 and the insulating shells 704A and 704B. The external electrode 746 may extend non-parallel (e.g., perpendicular) to the nanowire axis 714 to connect to external circuitry.

Figure 8B:
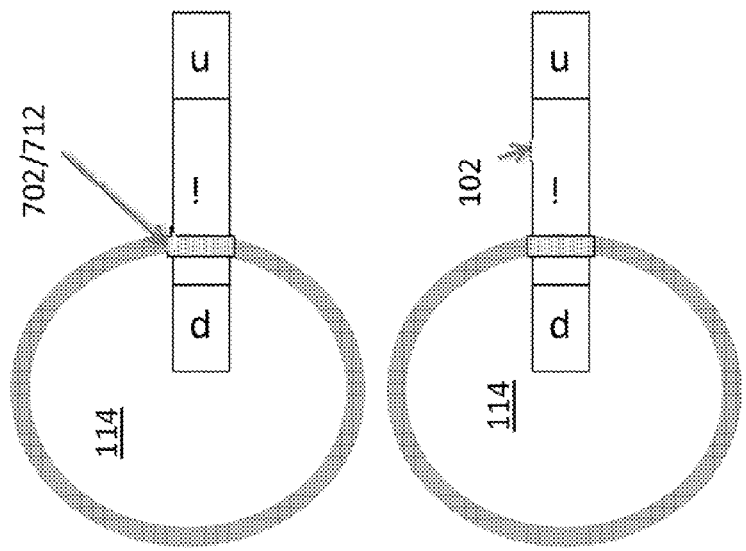
FIGS. 8A and 8B are schematic illustrations of a method of removing a biodegradable substrate from nanowires embedded into cells.
Figure 8A:
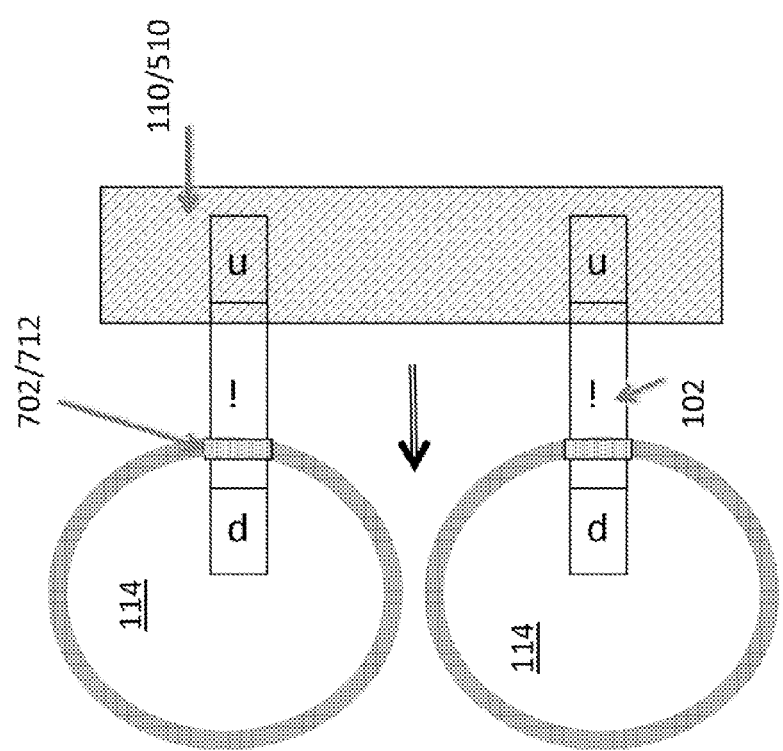

In one embodiment illustrated in FIG. 8A, the nanowire photovoltaic cell 102 has both a seal 702 or 712 and the substrate 110 or 510 is made of a biodegradable material. In this embodiment, the substrate material is selected such that the degradation of the biodegradable substrate material will last long enough to let the cells 114 (e.g., pierced neurons) form a GigaOhm seal around the nanowire hydrophobic seal 702 or 712, as shown in FIG. 8B, while tempering the immune response to the implant at the same time. After the substrate degradation, nanowire intracellular part 716 will be accessing the neuron cytosol. The nanowire part 716 will deliver current or voltage inside the cytosol and stimulate the neurons upon excitation by radiation. If desired, phospholipids may be adsorbed on the nanowire intracellular part 716 in order to facilitate the insertion inside the cell. Also, the predetermined height of the nanowire part inserted in the cell cytosol can be chosen in order to optimize cell stimulation Thus, the devices provide an intimate contact with the cells, providing an extremely high seal resistance on the order of at least one GigaOhm. The minimal dimensions of the nanowire electrode ensure that minimum power/current will be required to stimulate the neurons. The number of nanowire per cell can be adjusted so that cells are stimulated in an optimized way (e.g., depending on the bio-application, depending on the cell type, etc). Therefore, in the configuration of a GigaOhm seal between the nanowires and the cell membrane, the effect of a single or an ensemble of nanowires will cause a significant change in the cell membrane potential.

VI. Extracellular Use

Figure 9:
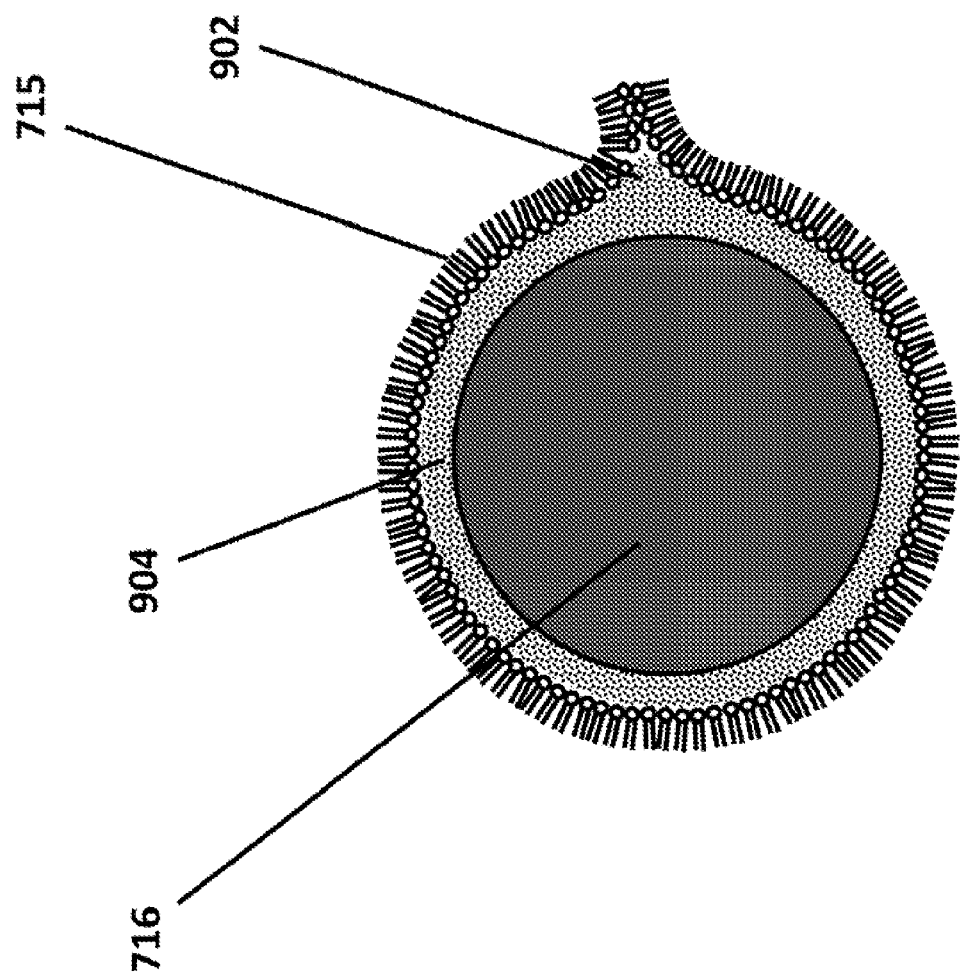
FIG. 9 is a schematic illustration of a nanowire-cell system in an extracellular configuration.

For extracellular stimulation, the nanowire intracellular part 716 (e.g., p-doped segment) surface may be functionalized with binding molecules or protein corona 904 that can bind the cellular membrane 715, ensuring a tight junction or seal 902 between the membrane and the nanowire, as illustrated in the FIG. 9. For example, a protein corona 904 might be used to bind the nanowire to the membrane because there is an indication that proteins adsorb on the nanowires when in biological medium, favoring cell adhesion. (see Piret G, et al., Neurite outgrowth and synaptophysin expression of postnatal CNS neurons on GaP nanowire arrays in long-term retinal cell culture, Biomaterials (available online Nov. 3, 2012 at http://dx.doi.org/10.1016/j.biomaterials.2012.10.042). Therefore all the current/voltage created by the nanowire will be applied across to cell membrane with no leak to the extracellular medium. The stimulation will be facilitated by the fact that the increase of membrane curvature around the nanowire is locally increasing the membrane conductance.

VII. Cell-Nanowire System Formation

Both extra- and intra-cellular configurations can be formed in vivo. The contact between the nanowires and the cells can be either mechanically forced or driven by self-assembly. The latter can result spontaneously from adhesion of the nanowire with the cell or from integration of a functionalized portion of the nanowire (e.g., a hydrophobic ring) with the cell membrane, both of which form a tight seal around the nanowire.

In another embodiment, the cell/nanowire system described above is formed in vitro. The cell/nanowire system described above can then be inserted or injected into tissue. Thus, to form the devices described above in the intracellular or extracellular configuration, the cells are first cultured on the array of nanowires, so that the cell and nanowire connection can be formed in a controlled fashion and in an optimal environment for cell culturing. This configuration could be used for basic studies of nanowire-cell interactions as well as for in vivo studies of the integration of a cell/nanowire device with the surrounding tissue. However, in the in vitro method, acceptance of both cells and nanowires puts much higher demands on bio and immune systems.

Thus, as described above, the cells form a tight seal around the nanowires in extra- or intra-cellular configuration. The cell and nanowire device form a bio-integrated device where cellular processes, such as release and inhibition of neurotransmitters, may be controlled through electrical stimulation from illumination or by electrical circuitry. The type of cells can be chosen freely according to function and availability by choice of cell type and cell functionality, and the response of the integrated device can be designed to support different functions in the body.

Although the foregoing refers to particular preferred embodiments, it will be understood that the invention is not so limited. It will occur to those of ordinary skill in the art that various modifications may be made to the disclosed embodiments and that such modifications are intended to be within the scope of the invention. All of the publications, patent applications and patents cited herein are incorporated herein by reference in their entirety.

What is claimed is:

1. A device, comprising:
    at least one photovoltaic cell and at least one nanowire configured to electrically stimulate a biological material in response to radiation, wherein the radiation is solar radiation or UV, visible or IR radiation from a lamp or laser;
    a hydrophobic seal located around a first portion of the nanowire, the hydrophobic seal exposing a protruding second portion of the nanowire configured as an intracellular electrode; and
    a first insulating shell located around the nanowire;
    wherein:
    the hydrophobic seal comprises an edge seal comprising a hydrophobic material shell located between the nanowire and the first insulating shell;
    the edge seal comprises an edge surface that extends substantially perpendicular to a longitudinal axis of the nanowire and that is exposed by the first insulating shell, for contacting the inside of a biological cell membrane.

2. The device of claim 1, wherein at least 50% of an outer radial surface of the edge seal is covered by the first insulating shell and the outer radial surface of the edge seal extends substantially parallel to the longitudinal axis of the nanowire.

3. The device of claim 2, wherein the edge seal comprises a 5 to 10 nm thick Au or Ni shell located between the first insulating shell and a second insulating shell.

4. The device of claim 3, wherein:
    the protruding second portion of the electrode protrudes outside the first and the second insulating shells and outside the edge seal.

5. The device of claim 4, further comprising at least one of a second electrode shell or a biocompatible barrier shell located around the second insulating shell.

6. The device of claim 4, wherein the edge surface is recessed with respect to the first insulating shell.

7. The device of claim 1, wherein:
    the at least one nanowire comprises a semiconductor nanowire which contains at least one of a p-type or n-type semiconductor regions of the at least one photovoltaic cell; and
    the at least one photovoltaic cell is inserted into or located adjacent to the biological material to directly provide electrical stimulation to the biological material.

8. The device of claim 7, wherein:
    the at least one photovoltaic cells comprises a semiconductor nanowire p-i-n or p-n photovoltaic cell;
    the nanowire comprises silicon, a III-V semiconductor material or a II-VI semiconductor material; and
    the nanowire comprises a coaxial nanowire in which the p-type and the n-type semiconductor regions are arranged coaxially or a longitudinal nanowire in which the p-type and the n-type semiconductor regions are arranged longitudinally.

9. The device of claim 8, wherein the electrical stimulation comprises an electrical current.

10. The device of claim 8, wherein the nanowire further comprises an insulating layer on the nanowire and the electrical stimulation comprises a voltage.

11. The device of claim 8, wherein the device is a neural probe.

12. The device of claim 5, wherein the device detects electrical or optical signals from the biological material.

13. The device of claim 6, wherein the at least one nanowire comprises a plurality of nanowires which are located on a growth substrate or are attached to a handle substrate different from the growth substrate.

14. A method of stimulating biological material using a device according to claim 1.

15. The method of claim 14, whereinthe photovoltaic cell is used as a neural device selected from a retinal implant, a neuroprotector or a DBS device.

16. The method of claim 14, further comprising inserting the photovoltaic cell into the biological cell membrane such that the edge surface of the edge seal contacts the inside of the biological cell membrane, wherein the edge surface of the edge seal extends substantially perpendicular to the longitudinal axis of the nanowire and is exposed by the first insulating shell which is located around the at least one nanowire when the photovoltaic cell is inserted into the biological cell membrane.

* * * * *